US012433981B2

(12) United States Patent
Fallman

(10) Patent No.: US 12,433,981 B2
(45) Date of Patent: Oct. 7, 2025

(54) PERITONEAL DIALYSIS SYSTEM HAVING PHASE CHANGE MATERIAL ("PCM") HEAT EXCHANGE

(71) Applicants: BAXTER INTERNATIONAL INC., Deerfield, IL (US); BAXTER HEALTHCARE SA, Glattpark (CH)

(72) Inventor: Oskar Erik Frode Styrbjorn Fallman, Lund (SE)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 18/715,519

(22) PCT Filed: Nov. 30, 2022

(86) PCT No.: PCT/US2022/080642
§ 371 (c)(1),
(2) Date: May 31, 2024

(87) PCT Pub. No.: WO2023/102414
PCT Pub. Date: Jun. 8, 2023

(65) Prior Publication Data

US 2024/0416019 A1 Dec. 19, 2024

Related U.S. Application Data

(60) Provisional application No. 63/285,233, filed on Dec. 2, 2021.

(51) Int. Cl.
*A61M 1/28* (2006.01)

(52) U.S. Cl.
CPC ..... *A61M 1/281* (2014.02); *A61M 2205/3646* (2013.01)

(58) Field of Classification Search
CPC .... A61M 1/153; A61M 1/1629; A61M 1/166; A61M 1/1662; A61M 1/1664;
(Continued)

(56) References Cited

U.S. PATENT DOCUMENTS 5,101,804 A * 4/1992 Cohn ...................... F24V 30/00 604/113
6,409,699 B1 * 6/2002 Ash ......................... A61M 1/32 604/29
(Continued)

OTHER PUBLICATIONS

International Search Report PCTUS2022080642 dated May 30, 2023—5 pages.
(Continued)

*Primary Examiner* — Kami A Bosworth
(74) *Attorney, Agent, or Firm* — K&L Gates LLP

(57) ABSTRACT

A peritoneal dialysis ("PD") system includes a PD fluid pump, a PD fluid heater positioned and arranged to heat fresh PD fluid pumped by the PD fluid pump, and a phase change material ("PCM") device positioned and arranged to receive fresh PD fluid heated by the PD fluid heater. The PCM device includes a PCM having a melting temperature selected so that the PCM solidifies when underheated fresh PD fluid contacts the PCM transferring heat to the underheated fresh PD fluid. Alternatively or additionally, the PD system may include a different PCM device having a PCM with a melting temperature selected so that the PCM melts when overheated fresh PD fluid contacts the PCM thereby removing heat from the overheated fresh PD fluid. A configuration for the PCM device is also disclosed.

22 Claims, 6 Drawing Sheets

(58) Field of Classification Search
CPC ........ A61M 1/28; A61M 1/281; A61M 1/282; A61M 1/284; A61M 5/44; A61M 5/445; A61M 2205/127; A61M 2205/36; A61M 2205/3646; A61M 2205/366
See application file for complete search history.

(56) References Cited

U.S. PATENT DOCUMENTS

| | | | | |
|---|---|---|---|---|
| 2006/0271014 | A1* | 11/2006 | Hynes | A61M 5/445 206/364 |
| 2008/0039815 | A1* | 2/2008 | Ogawa | A61M 5/44 604/408 |
| 2011/0319813 | A1* | 12/2011 | Kamen | A61M 5/5086 604/151 |
| 2013/0226087 | A1* | 8/2013 | King | A61M 5/44 604/113 |
| 2016/0271342 | A1* | 9/2016 | Bronkhorst | F24H 9/2028 |
| 2017/0319768 | A1 | 11/2017 | Szpara et al. | |
| 2017/0333630 | A1* | 11/2017 | Van Oudenallen | A61M 5/445 |
| 2018/0333330 | A1 | 11/2018 | Nagar | |
| 2020/0038600 | A1* | 2/2020 | Bitton | G16H 20/17 |
| 2020/0080789 | A1 | 3/2020 | Quinn | |
| 2022/0184286 | A1* | 6/2022 | Leven | A61M 1/28 |

OTHER PUBLICATIONS

Written Opinion PCTUS2022080642 dated May 30, 2023—5 pages.
International Preliminary Report on Patentability—PCT/US2022/080642 dated May 2, 2024—13 pages.

* cited by examiner

PERITONEAL DIALYSIS SYSTEM HAVING PHASE CHANGE MATERIAL ("PCM") HEAT EXCHANGE

PRIORITY CLAIM

The present application is a national phase entry of PCT Patent Application No. PCT/US2022/080642, filed on Nov. 30, 2022, which claims priority to and the benefit of U.S. Provisional Application No. 63/285,233, filed Dec. 2, 2021, the entire contents of which are herein incorporated by reference and relied upon.

BACKGROUND

The present disclosure relates generally to medical fluid treatments and in particular to the filtering of treatment fluid during dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid or PD fluid, into a patient's peritoneal chamber via a catheter. The PD fluid comes into contact with the peritoneal membrane in the patient's peritoneal chamber. Waste, toxins and excess water pass from the patient's bloodstream, through the capillaries in the peritoneal membrane, and into the PD fluid due to diffusion and osmosis, i.e., an osmotic gradient occurs across the membrane. An osmotic agent in the PD fluid provides the osmotic gradient. Used PD fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used PD fluid to drain from the patient's peritoneal cavity. The patient then switches fluid communication so that the patient catheter communicates with a bag of fresh PD fluid to infuse the fresh PD fluid through the catheter and into the patient. The patient disconnects the catheter from the fresh PD fluid bag and allows the PD fluid to dwell within the patient's peritoneal cavity, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

APD is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh PD fluid and to a fluid drain. APD machines pump fresh PD fluid from a dialysis fluid source, through the catheter and into the patient's peritoneal chamber. APD machines also allow for the PD fluid to dwell within the chamber and for the transfer of waste, toxins and excess water to take place. The source may include multiple liters of dialysis fluid, including several solution bags. APD machines pump used PD fluid from the patient's peritoneal cavity, though the catheter, to drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

APD machines also heat the fresh PD fluid, e.g., to body temperature, before delivering same to the patient. There can be several drawbacks with the heating of the fresh PD fluid. Batch heating for example takes time and requires a relatively large space for the heater. Inline heating is subject to underheating and overheating of the fresh PD fluid. Underheating typically occurs at the beginning of a patient fill, where the fluid circuit may be relatively cold and the control of the inline heater has not yet steadied. Regarding overheating, inline heaters are subject to temperature spikes when fresh PD fluid flow is temporarily stopped or drastically slowed. In such cases, energy is transferred from the inline heater to the still standing fresh PD fluid, resulting potentially in an overheated PD fluid.

Another problem with a PD fluid treatment in general, regardless of batch or inline heating, is that effluent or used PD fluid removed from the patient is typically at body temperature or 37° C., which is above ambient temperature. Used PD fluid is typically discarded to drain and thus its elevated temperature is wasted.

In light of the above-described problems, an APD system having improved PD fluid heating is needed accordingly.

SUMMARY

The present disclosure provides a peritoneal dialysis ("PD") system having improved fresh PD fluid heating and in particular improved inline PD fluid heating. The PD system includes a PD machine or cycler that pumps fresh PD fluid through a patient line to a patient and removes used PD fluid from the patient via the patient line. The patient line may be reusable or disposable.

The PD machine or cycler may include a durable PD fluid pump that pumps PD fluid through the pump itself without using a disposable component, or a disposable type PD fluid pump including a pump actuator that actuates a disposable, fluid-contacting pumping component, such as a peristaltic pump tube or a flexible pumping chamber. It should be appreciated that while a single PD fluid pump may be used, dedicated fresh and used PD fluid pumps may be used alternatively. Also, a single PD fluid pump may include multiple pumping chambers for more continuous PD fluid flow.

The PD machine or cycler also includes a plurality of valves, which may likewise be flow-through and durable without operating with a disposable component, or be disposable type valves having valve actuators that actuate a disposable, fluid-contacting valve component, such as a tube segment or a cassette-based valve seat. In an embodiment, the valves include, among many others, a fresh PD fluid valve that the control unit opens to allow the PD fluid pump to pump fresh PD fluid through a fresh PD fluid lumen of a dual lumen patient line to the patient. The valves also include a used PD fluid valve that the control unit opens to allow the PD fluid pump to pump used PD fluid from the patient through a used PD fluid lumen of the dual lumen patient line.

The PD machine or cycler includes a PD fluid heater, which in one embodiment is an inline PD fluid heater. A temperature sensor is placed downstream from the inline PD fluid heater, the output of which is used for feedback control of the inline PD fluid heater, e.g., proportional, integral, derivative ("PID") control. In other embodiments, a model-based approach may be used for the feedback control of the inline PD fluid heater. An additional temperature sensor may be located upstream of the inline heater for feedforward control. In an embodiment, it is attempted to have the inline PD fluid heater heat the fresh PD fluid to body temperature or 37° C., with a lower temperature limit of 32° C. and an upper temperature limit of 41° C. At least one further additional temperature sensor may be located downstream from any one or more of the phase change material devices discussed herein to assess its/their effect on PD fluid temperature.

The pumps, valves and inline PD fluid heater are under the automatic control of a control unit provided by the machine or cycler. The control unit also receives outputs from sensors, such as pressure sensors and one or more temperature sensor. The control unit further uses the outputs from the sensors as feedback for pump and heater control, e.g., as mentioned above for the control of inline PD fluid heater.

The PD machine or cycler of the PD system of the present disclosure also includes one or more phase change material ("PCM") device used to perform at least one of: (i) mitigating underheating by the inline PD fluid heater, e.g., at the beginning of a patient fill, (ii) mitigating overheating by the inline PD fluid heater, e.g., due to a stoppage or severe slowing of fresh PD fluid flow, and (iii) recouping heat from effluent or used PD fluid flow removed from the patient. The PCM devices of the present disclosure store thermal energy by the phase change from solid to liquid. In an embodiment, the PCM's used in the devices of the present disclosure require a relatively large amount of energy to undergo the solid-to-liquid phase change. The energy required to transition between solid and liquid phases is known as the latent heat of fusion. The PCM's used herein have a high latent heat of fusion and can therefore store a significant amount of heat during a phase transition, while maintaining a near constant temperature around the PCM's melting temperature. Different PCM's for the different uses (i) to (iii) above are chosen to have a desired melting temperature for that use.

The melting temperature in an embodiment dictates the material and type of PCM suitable for use in the system of the present disclosure. Because the melting temperatures needed here are relatively low, paraffin or paraffin blend waxes and non-paraffin organics are suitable because they are relatively inexpensive and remain stable through many thermal cycles. Paraffins (paraffin blends) and non-paraffin organics are suitable PCM's because they melt and freeze congruently (have the same composition before and after freezing) and therefore provide material stability through many treatments, making the PCM devices of the present disclosure largely reusable.

A drawback of paraffin (paraffin blend) and non-paraffin organic PCM's is their thermal conductivity, which may be around 0.2 W/m-K. It is accordingly contemplated to form or place the PCM within a series or matrix of conductive heat fins, which are non-PD fluid contacting, such that the heat fins may be of a highly thermally conductive material, such as aluminum or copper. The heat fins also hold the PCM in place when in its liquid form, so that it will freeze back into generally the same shape abutting against the heat fins. The heat fins in turn contact a metal suitable for contacting a flow of medical, e.g., PD, fluid, such as stainless steel. The PD fluid may for example flow outside of or inside of a stainless steel tube, wherein the PCM and heat fin matrix is located inside or outside, respectively, of the tube. An outer tube may then be provided to complete the PCM device of the present disclosure along with a PD fluid inlet and a PD fluid outlet. The outer tube may be thermally in conductive, e.g., metal, or be thermally insulating, e.g., plastic, based on the application of the PCM device in the PD system of the present disclosure. And as discussed herein, the PCM device of the PD system of the present disclosure may include one or more heating element, e.g., in thermal communication with the heat fin matrix, to melt the PCM prior to a use application in which PD fluid is to be heated.

It is contemplated for the embodiment in which underheating by the inline PD fluid heater is mitigated, e.g., at the beginning of a patient fill, that the PCM device be placed between the inline PD fluid heater and the downstream temperature sensor, so that the temperature increasing effect from the PCM device is detected or recorded by the downstream temperature sensor. To increase the temperature of underheated fresh PD fluid, the PCM device prior to the patient fill is heated and melted. The melting temperature for the underheated fluid PCM device is in one embodiment 32° C. to 34° C. Here, the fresh PD fluid flowing past the melted underheated fluid PCM device at a temperature lower than 32° C. to 34° C. will freeze the melted PCM, releasing the latent heat from the PCM and warming the fresh PD fluid to the melting temperature, e.g., 32° C. to 34° C.

As the inline fluid heating stabilizes and begins to output fresh PD fluid closer to the commanded temperature of 37° C., the underheated fluid PCM device remelts, pulling latent heat into the device. The PCM device accordingly creates a lag in PD fluid temperature. Eventually, the PCM is fully melted and thereafter has no effect on PD fluid temperature unless the temperature during the patient fill for some reason falls again below the melting temperature for the underheated fluid PCM device, e.g., 32° C. to 34° C.

As stated above, the PCM for the underheated fluid PCM device is heated and melted prior to beginning the patient fill. It is contemplated to do this in a plurality of different ways. In one way, the underheated fluid PCM device is provided with one or more heating element positioned to heat the heat fins, which in turn heats and melts the PCM prior to a patient fill. In a second way, which may be performed for a first patient fill, which does not follow an initial patient drain or wherein a dual lumen patient line is used, the system heats the priming fluid and flows the heated priming fluid through the underheated fluid PCM device to melt the PCM prior to a first patient fill. In a third way, which may be performed for a first patient fill, which does follow an initial patient drain, or for any subsequent fill which follows a patient drain, the system recovers heat from the patient's effluent or used PD fluid. The patient's effluent, which typically has a body temperature, e.g., 37° C., is flowed through the underheated fluid PCM device to melt the PCM prior to the subsequent patient fill.

It is likewise contemplated for the embodiment in which overheating by the inline PD fluid heater is mitigated, e.g., during a no or low PD fluid flow condition, that the PCM device also be placed between the inline PD fluid heater and the downstream temperature sensor, so that the temperature decreasing effect from the PCM device is detected or recorded by the downstream temperature sensor. To decrease the temperature of overheated fresh PD fluid, the PCM device melts to absorb latent heat, thereby lowering the temperature of the fresh PD fluid. The melting temperature for the overheated fluid PCM device is in one embodiment 37° C. but could be higher if a slight overtemperature is acceptable, e.g., to reduce the amount of thermal cycles to which the PCM device is subjected. Here, the fresh PD fluid flowing past the solid overheated fluid PCM device at a temperature greater than 37° C. (or higher setpoint) melts its PCM, causing heat to be stored by the PCM and cooling the fresh PD fluid to the melting temperature, e.g., 37° C. or higher.

It is contemplated for the embodiment in which it is desired to remove heat from the patient's effluent or used PD fluid, e.g., to produce an overall more energy efficient PD system, to locate the PCM device along the effluent or used PD fluid return line from the patient to drain. The recover effluent energy PCM device operates in the same manner as the overheated fluid PCM device, wherein the PCM melts from a solid to a liquid to remove heat from the PD fluid and absorb the latent heat within the PCM. Here, however, the melting temperature of the recover effluent energy PCM device is lower, e.g., 32° C. to 34° C., so that the PCM is melted by the patient's effluent, which is at body temperature or 37° C. The recover effluent energy PCM device is also located so that it may later receive fresh PD fluid to transfer the stored latent heat to the fresh PD fluid, thereby recovering and returning energy from the effluent fluid.

The recover effluent energy PCM device may alternatively be located within the PD machine or cycler upstream of the inline PD fluid heater. Locating PCM device upstream of the inline PD fluid heater allows the melting temperature of the corresponding PCM to be considerably lower, e.g., 25° C. to 30° C., increasing the amount of latent energy that may be stored from the flowing patient effluent (and later recovered), wherein the effluent fluid may be at or near body temperature or 37° C. During a next patient fill, fresh, unheated PD fluid at a known or expected temperature below the PCM melting temperature (e.g., 25° C. to 30° C.), causes the melted PCM to start to solidify, giving off heat and warming the incoming fresh PD fluid.

It is further contemplated for the PD system of the present disclosure to provide a combination of the underheated fluid PCM device, the overheated fluid PCM device and the recover effluent energy PCM device. In one embodiment, the underheated fluid PCM device and the recover effluent energy PCM device are the same PCM device having the same melting temperature, e.g., 32° C. to 34° C. The same PCM device for addressing underheating is used at a time when the PCM has been melted and is in condition to return latent heat. The same PCM device for recovering effluent energy is used at a time when the PCM is in solid form and is in condition to absorb latent heat from used PD fluid to melt and thereby be ready to return latent heat to underheated fresh PD fluid.

The overheated fluid PCM device is separate from the dual function PCM device and has a different melting temperature, e.g., 37° C. of higher. For a PD system of the present disclosure having a dual lumen patient line, the overheated fluid PCM device is located in one embodiment so as to only see fresh PD fluid that flows through a fresh PD fluid lumen leading to the patient.

In an alternative embodiment, the PCM device for recovering effluent energy is formed as a separate PCM device and is located upstream of the inline PD fluid heater. Locating the PCM device for recovering effluent energy upstream of the inline PD fluid heater allows the melting temperature of the corresponding PCM to be considerably lower, e.g., 25° C. to 30° C., which increases the amount of latent energy that may be stored from the flowing patient effluent (and later recovered), wherein the effluent fluid may be at or near body temperature or 37° C.

In a further alternative embodiment, the PCM device for recovering effluent energy is formed instead as a heater exchanger. The heat exchanger may be provided with an outer insulting (e.g., plastic or fiberglass) shell that holds two conductive, e.g., stainless steel tubes, one for carrying fresh PD fluid and the other for carrying used PD fluid. PCM material having the desired melting temperature, e.g., 25° C. to 30° C., for recovering effluent energy is then provided within the insulating shell and around the outsides of the fresh and used PD fluid tubes, which may be juxtaposed in parallel. The heat exchanger works even when the fresh and used PD fluids do not flow at the same time because the insulated PCM material stores the latent heat energy absorbed from the effluent fluid until fresh PD fluid is flowed through its tube in a next patient fill. In one embodiment, the PD machine or cycler is programmed to begin the next patient fill directly after the completion of a patient drain to reduce overall treatment time, which helps the PCM material to hold the latent heat energy until it can be transferred to incoming fresh PD fluid.

In light of the disclosure set forth herein, and without limiting the disclosure in any way, in a first aspect of the present disclosure, which may be combined with any other aspect, or portion thereof, a peritoneal dialysis ("PD") system includes a PD fluid pump; a PD fluid heater positioned and arranged to heat fresh PD fluid pumped by the PD fluid pump; and a phase change material ("PCM") device positioned and arranged to receive fresh PD fluid heated by the PD fluid heater, the PCM device including a PCM having a melting temperature selected so that the PCM solidifies when underheated fresh PD fluid contacts the PCM, transferring heat to the underheated PD fluid.

In a second aspect of the present disclosure, which may be combined with any other aspect, or portion thereof, the PD fluid heater is an inline heater.

In a third aspect of the present disclosure, which may be combined with any other aspect, or portion thereof, the melting temperature for the PCM is below 37° C., such as 32° C. to 34° C.

In a fourth aspect of the present disclosure, which may be combined with any other aspect, or portion thereof, the underheated fresh PD fluid is PD fluid having a temperature below the melting temperature.

In a fifth aspect of the present disclosure, which may be combined with any other aspect, or portion thereof, the PD system is configured to melt the PCM prior to the underheated fresh PD fluid contacting the PCM, the melting caused by (i) one or more heating element provided with the PCM device for heating the PCM, (ii) flowing heated priming fluid past the PCM, or (iii) flowing used PD fluid past the PCM.

In a sixth aspect of the present disclosure, which may be combined with any other aspect, or portion thereof, wherein in (ii) and (iii), the PCM device separates the PCM from the heated priming fluid or the used PD fluid, respectively, via a conductive wall.

In a seventh aspect of the present disclosure, which may be combined with any other aspect, or portion thereof, the PCM device is also positioned to receive used PD fluid, the melting temperature of the PCM device selected so that the PCM melts when the used PD fluid contacts the PCM, removing heat from the used PD fluid.

In an eighth aspect of the present disclosure, which may be combined with any other aspect, or portion thereof, the PD system includes a bypass line enabling the used PD fluid to bypass the PD fluid heater.

In a ninth aspect of the present disclosure, which may be combined with any other aspect, or portion thereof, the PD system includes a dual lumen patient line, and wherein a PD machine housing the PD fluid pump, the PD fluid heater and the PCM device further includes (i) a fresh PD fluid line for fluid communication with a fresh PD fluid lumen of the dual lumen patient line, (ii) a used PD fluid line for fluid communication with a used PD fluid lumen of the dual lumen patient line, and (iii) at least one valve positioned and arranged to selectively allow (a) fresh PD fluid to flow through the PCM device, the fresh PD fluid line and the fresh PD fluid lumen and (b) used PD fluid to flow through the used PD fluid lumen, the used PD fluid line and the PCM device.

In a tenth aspect of the present disclosure, which may be combined with any other aspect, or portion thereof, the PD system includes a single lumen patient line, and wherein a PD machine housing the PD fluid pump, the PD fluid heater and the PCM device further includes a fresh and used PD fluid line for fluid communication with the single lumen patient line, the fresh and used PD fluid line positioned and arranged to accept fresh PD fluid from the PCM device and deliver used PD fluid to the PCM device.

In an eleventh aspect of the present disclosure, which may be combined with any other aspect, or portion thereof, the PCM device is a first PCM device, and which includes a second PCM device including a second PCM having a second melting temperature selected so that the second PCM melts when overheated fresh PD fluid contacts the second PCM, removing heat from the overheated fresh PD fluid.

In a twelfth aspect of the present disclosure, which may be combined with any other aspect, or portion thereof, the second PCM device is located downstream from the first PCM device regarding fresh PD fluid flow.

In a thirteenth aspect of the present disclosure, which may be combined with any other aspect, or portion thereof, the melting temperature for the second PCM is 37° C. or higher.

In a fourteenth aspect of the present disclosure, which may be combined with any other aspect, or portion thereof, the PCM device is positioned upstream of the PD fluid heater so as to receive used PD fluid, the melting temperature of the PCM device selected so that the PCM melts when the used PD fluid contacts the PCM, removing heat from the used PD fluid.

In a fifteenth aspect of the present disclosure, which may be combined with any other aspect, or portion thereof, the melting temperature of the PCM device is 25° C. to 30° C.

In a sixteenth aspect of the present disclosure, which may be combined with any other aspect, or portion thereof, a peritoneal dialysis ("PD") system includes a PD fluid pump; a PD fluid heater positioned and arranged to heat fresh PD fluid pumped by the PD fluid pump; and a phase change material ("PCM") device positioned and arranged to receive fresh PD fluid heated by the PD fluid heater, the PCM device including a PCM having a melting temperature selected so that the PCM melts when overheated fresh PD fluid contacts the PCM, removing heat from the overheated fresh PD fluid.

In a seventeenth aspect of the present disclosure, which may be combined with any other aspect, or portion thereof, the melting temperature for the PCM is 37° C. or higher.

In an eighteenth aspect of the present disclosure, which may be combined with any other aspect, or portion thereof, the overheated fresh PD fluid is PD fluid having a temperature above the melting temperature.

In a nineteenth aspect of the present disclosure, which may be combined with any other aspect, or portion thereof, the PD system includes a dual lumen patient line, and wherein a PD machine housing the PD fluid pump, the PD fluid heater and the PCM device further includes (i) a fresh PD fluid line for fluid communication with a fresh PD fluid lumen of the dual lumen patient line, and (ii) a used PD fluid line for fluid communication with a used PD fluid lumen of the dual lumen patient line, wherein the PCM device is located along or in fluid communication with the fresh PD fluid line.

In a twentieth aspect of the present disclosure, which may be combined with any other aspect, or portion thereof, the PD system includes a single lumen patient line, wherein a PD machine housing the PD fluid pump, the PD fluid heater and the PCM device further includes a fresh and used PD fluid line for fluid communication with the single lumen patient line, and wherein the PCM device is located along or in fluid communication with the fresh and used PD fluid line.

In a twenty-first aspect of the present disclosure, which may be combined with any other aspect, or portion thereof, a peritoneal dialysis ("PD") system includes a PD fluid pump; a PD fluid heater positioned and arranged to heat fresh PD fluid pumped by the PD fluid pump; and a phase change material ("PCM") device positioned and arranged to receive used PD fluid returning from a patient, the PCM device including a PCM having a melting temperature selected so that the PCM melts when the used PD fluid contacts the PCM, removing heat from the used PD fluid.

In a twenty-second aspect of the present disclosure, which may be combined with any other aspect, or portion thereof, the melting temperature for the PCM is below 37° C., such as 32° C. to 34° C.

In a twenty-third aspect of the present disclosure, which may be combined with any other aspect, or portion thereof, the used PD fluid has a patient body temperature.

In a twenty-fourth aspect of the present disclosure, which may be combined with any other aspect, or portion thereof, the PD system includes a dual lumen patient line, and wherein a PD machine housing the PD fluid pump, the PD fluid heater and the PCM device further includes (i) a fresh PD fluid line for fluid communication with a fresh PD fluid lumen of the dual lumen patient line, (ii) a used PD fluid line for fluid communication with a used PD fluid lumen of the dual lumen patient line, and (iii) at least one valve positioned and arranged to selectively allow (a) fresh PD fluid to flow through the PCM device, the fresh PD fluid line and the fresh PD fluid lumen and (b) used PD fluid to flow through the used PD fluid lumen, the used PD fluid line and the PCM device.

In a twenty-fifth aspect of the present disclosure, which may be combined with any other aspect, or portion thereof, the PD system includes a single lumen patient line, wherein a PD machine housing the PD fluid pump, the PD fluid heater and the PCM device further includes a fresh and used PD fluid line for fluid communication with the single lumen patient line, and wherein the PCM device is located along or in fluid communication with the fresh and used PD fluid line.

In a twenty-sixth aspect of the present disclosure, which may be combined with any other aspect, or portion thereof, at least one of (i) the PCM device is positioned upstream of the PD fluid heater or (ii) the melting temperature of the PCM device is 25° C. to 30° C.

In a twenty-seventh aspect of the present disclosure, which may be combined with any other aspect, or portion thereof, the PCM device is a heat exchanger configured to receive fresh and used PD fluid, the PCM positioned and arranged within the heat exchanger to contact both a fresh PD fluid tube for carrying the fresh PD fluid and a used PD fluid tube for carrying the used PD fluid.

In a twenty-eighth aspect of the present disclosure, which may be combined with any other aspect, or portion thereof, the PCM is located within an insulating shell of the heat exchanger, wherein the fresh and used PD fluid tubes are conductive, and wherein the PCM is located within the insulating shell so as to contact the conductive fresh and used PD fluid tubes.

In a twenty-ninth aspect of the present disclosure, which may be combined with any other aspect, or portion thereof, a phase change material ("PCM") device includes a PCM having a melting temperature of (i) below 37° C., such as 32° C. to 34° C., for heating underheated fresh peritoneal dialysis ("PD") fluid or for cooling used PD fluid or (ii) 37° C. or higher for cooling overheated fresh PD fluid; a conductive wall holding the PCM; and a shell creating a peritoneal dialysis ("PD") fluid pathway with the conductive wall, the shell including a plurality of ports for allowing fresh or used PD fluid into and out of the PD fluid pathway.

In a thirtieth aspect of the present disclosure, which may be combined with any other aspect, or portion thereof, the PCM device includes a plurality of conductive heat fins contacting the PCM, the conductive heat fins in thermal contact with the conductive wall.

In a thirty-first aspect of the present disclosure, which may be combined with any other aspect, or portion thereof, the conductive wall and the shell are at least substantially cylindrical.

In a thirty-second aspect of the present disclosure, which may be combined with any other aspect, or portion thereof, the shell is located outside of the conductive wall.

In a thirty-third aspect of the present disclosure, which may be combined with any other aspect, or portion thereof, the PCM device includes at least one baffle extending into the PD fluid pathway for disrupting the flow of fresh or used PD fluid.

In a thirty-fourth aspect of the present disclosure, which may be combined with any other aspect, or portion thereof, the plurality of ports are each inlet and outlet ports.

In a thirty-fifth aspect of the present disclosure, which may be combined with any other aspect, or portion thereof, the PCM device includes one or more heating element for heating the PCM.

In a thirty-sixth aspect of the present disclosure, which may be combined with any other aspect, or portion thereof, any of the features, functionality and alternatives described in connection with any one or more of FIGS. 1A to 6B may be combined with any of the features, functionality and alternatives described in connection with any other of FIGS. 1A to 6B.

In light of the above aspects and the description herein, it is an advantage of the present disclosure to provide a PD system having inline heating, wherein initial underheating is mitigated.

It is another advantage of the present disclosure to provide a PD system having inline heating, wherein overheating is mitigated.

It is a further advantage of the present disclosure to provide a PD system having inline heating, wherein at least one of underheating and overheating is mitigated without the need for additional temperature sensing and associated feedback control.

It is yet another advantage of the present disclosure to provide a PD system that is able to recoup heat from effluent or used PD fluid removed from the patient.

It is still a further advantage of the present disclosure to provide a PD system having improved inline heating using one or more phase change material ("PCM") device.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1A:
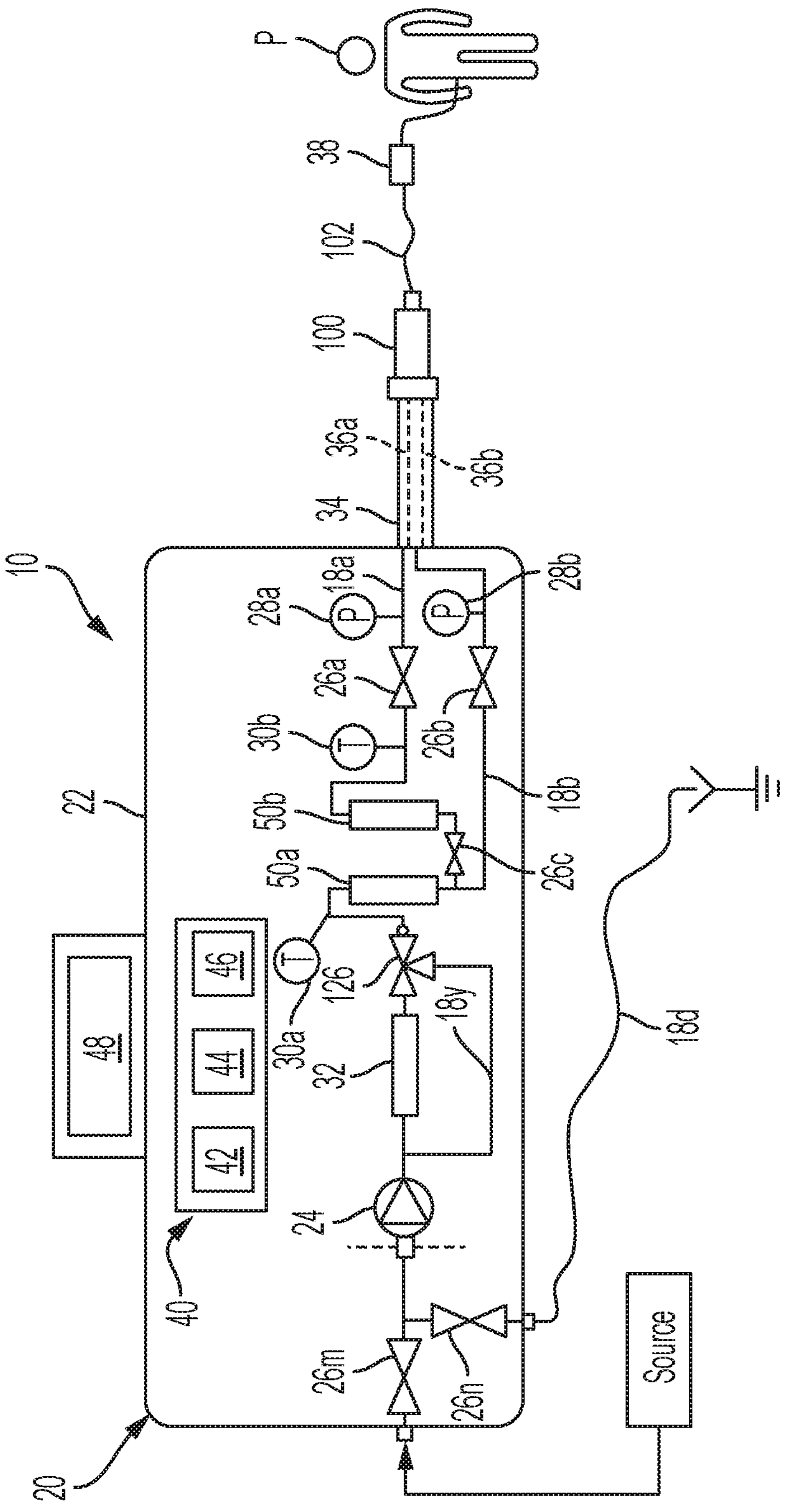
FIG. 1A is a schematic view of one embodiment for a dual lumen patient line peritoneal dialysis system having at least one phase change material ("PCM") device of the present disclosure.

Referring now to the drawings and in particular to FIG. 1A, a peritoneal dialysis ("PD") system 10 is illustrated. PD system 10 includes a PD machine or cycler 20 that pumps fresh PD fluid through a patient line 34 to a patient P and removes used PD fluid from patient P via patient line 34. Patient line 34 may be reusable or disposable and may operate with a sterilizing grade filter set 100, e.g., to allow the flowpaths of cycler 20 to be disinfected between uses. If patient line 34 is reusable, the reusable patient line is connected to sterilizing grade filter set 100 at the time of treatment. If patient line 34 is instead disposable, sterilizing grade filter set 100 is merged into or formed with disposable patient line 34 in one embodiment. In either configuration, a distal end of sterilizing grade filter set 100 may be connected to the patient's transfer set 38, which in turn communicates fluidly with the indwelling catheter of patient P.

PD machine or cycler 20 may include a housing 22 providing a durable PD fluid pump 24 that pumps PD fluid through the pump itself without using a disposable component. Examples of durable pumps that may be used for PD fluid pump 24 include piston pumps, gear pumps and centrifugal pumps. Certain durable pumps, such as piston pumps are inherently accurate, so that machine or cycler 20 does not require additional volumetric control components. Other durable pumps, such as gear pumps and centrifugal pumps may not be as accurate, such that machine or cycler 20 provides a volumetric control device such as one or more flowmeter (not illustrated).

Pump 24 may alternatively be a disposable type PD fluid pump, which includes a pump actuator that actuates a disposable, fluid-contacting pumping component, such as a peristaltic pump tube or a flexible pumping chamber. Examples of disposable PD fluid pumps that may be used for PD fluid pump 24 include rotary or linear peristaltic pump actuators that actuate tubing, pneumatic pump actuators that actuate cassette sheeting, electromechanical pump actuators that actuate cassette sheeting and platen pump actuators that actuate tubing. It should be appreciated that while a single PD fluid pump 24 may be used, dedicated fresh and used PD fluid pumps may be used alternatively. Also, single PD fluid pump 24 may include multiple pumping chambers for more continuous PD fluid flow.

PD machine or cycler 20 also includes a plurality of valves 26*a*, 26*b*, 26*c*, 26*m*, 26*n*, 126 which may likewise be flow-through and durable without operating with a disposable component, or be disposable type valves having valve actuators that actuate a disposable, fluid-contacting valve component, such as a tube segment or a cassette-based valve seat. Examples of durable valves that may be used for valves 26*a*, 26*b*, 26*c*, 26*m*, 26*n*, 126 include flow-through solenoid valves. Such valves may be two-way (26*a*, 26*b*, 26*c*, 26*m*, 26*n*) or three-way (126) valves. Examples of disposable valves that may be used for two-way valves 26*a*, 26*b*, 26*c*, 26*m*, 26*n* include solenoid pinch valves that pinch closed flexible tubing, pneumatic valve actuators that actuate cassette sheeting, and electromechanical valve actuators that actuate cassette sheeting.

Machine or cycler 20 likely includes many valves 26*a* to 26*n*. For ease of illustration, machine or cycler 20 is shown having a fresh PD fluid valve 26*a* that is controlled to open to allow PD fluid pump 24 to pump fresh PD fluid under positive pressure through a fresh PD fluid lumen 36*a* of dual lumen patient line 34 to patient P. The valves also include a used PD fluid valve 26*b* that is controlled to open to allow PD fluid pump 24 to pull used PD fluid from patient P under negative pressure through a used PD fluid lumen 36*b* of dual lumen patient line 34. The valves further include a valve 26*c* that is controlled to either allow fresh PD fluid to flow through phase change material ("PCM") device 50*a* (valve 26*c* open, valve 26*b* closed) or used PD fluid to flow through PCM device 50*a* (valve 26*c* closed, valve 26*b* open). The valves still further include three-way valve 126, which either allows fresh, heated PD fluid to flow to PCM device 50*a* or used PD fluid to bypass PD fluid heater 32 via bypass line 18*y* on its way to PD fluid pump 24. The valves additionally include one or more supply valve 26*m* that is controlled to open to allow fresh PD fluid to be pulled from one or more fresh PD fluid source. Moreover, the valves include a drain valve 26*n* that is controlled to allow used PD fluid to be delivered to a house drain or drain container via a drain line 18*d*.

Machine or cycler 20 in the illustrated embodiment also includes pressure sensors, such as pressure sensors 28*a*, 28*b*. Pressure sensor 28*a* is located just downstream from fresh PD fluid valve 26*a*, while pressure sensor 28*b* is located just upstream from used PD fluid valve 26. Pressure sensor 28*a* may accordingly sense the pressure in fresh PD fluid lumen 36*a* of dual lumen patient line 34 even if fresh PD fluid valve 26*a* is closed, while pressure sensor 28*b* may sense the pressure in used PD fluid lumen 36*b* of dual lumen patient line 34 even if used PD fluid valve 26*b* is closed.

Pump 24 and valves 26*a*, 26*b*, 26*c*, 26*m*, 26*n*, 126 in the illustrated embodiment are under the automatic control of a control unit 40 provided by machine or cycler 20 of system 10, while pressure sensors 28*a*, 28*b*, temperature sensors 30*a*, 30*b* (and other sensors) output to control unit 40. Control unit 40 in the illustrated embodiment includes one or more processor 42, one or more memory 44 and a video controller 46. Control unit 40 receives, stores and processes signals or outputs from pressure sensors 28*a*, 28*b*, and other sensors provided by machine or cycler 20, such as one or more temperature sensor 30*a*, 30*b* and one or more conductivity sensor (not illustrated). Control unit 40 may use pressure feedback from one or more of pressure sensor 28*a*, 28*b* to control PD fluid pump 24 to pump dialysis fluid at a desired pressure and within a safe pressure limits (e.g., within 0.21 bar (three psig) of positive pressure to a patient's peritoneal cavity and −0.10 bar (−1.5 psig) of negative pressure from the patient's peritoneal cavity).

Control unit 40 uses temperature feedback from temperature sensor 30*a,* for example, to control a PD fluid heater 32, such as an inline heater to heat fresh PD fluid to a desired temperature, e.g., body temperature or 37° C. PID control or a model-based approach may be used to provide the feedback control. An additional temperature sensor (not illustrated) may be provided upstream of PD fluid heater 32, which outputs to control unit 40 for feedforward control of the PD fluid heater. In one embodiment, inline PD fluid heater 32 is used additionally to heat a disinfection fluid, such as fresh PD fluid, to disinfect PD fluid pump 24, valves 26*a,* 26*b,* 26*c,* 26*m,* 26*n,* 126, heater 32 and all reusable fluid lines within machine or cycler 20 to ready the machine or cycler for a next treatment.

Video controller 46 of control unit 40 interfaces with a user interface 48 of machine or cycler 20, which may include a display screen operating with a touchscreen and/or one or more electromechanical button, such as a membrane switch. User interface 48 may also include one or more speaker for outputting alarms, alerts and/or voice guidance commands. User interface 48 may be provided with the machine or cycler 20 as illustrated in FIG. 1A and/or be a remote user interface operating with control unit 40. Control unit 40 may also include a transceiver (not illustrated) and a wired or wireless connection to a network, e.g., the internet, for sending treatment data to and receiving prescription instructions from a doctor's or clinician's server interfacing with a doctor's or clinician's computer.

FIG. 1A further illustrates fresh and used PD fluid lumens 36*a* and 36*b* of dual lumen patient line 34 extend to sterilizing grade filter set 100. A short, flexible tube 102 extends form sterilizing grade filter set 100 to the patient's transfer set 38. In an alternative embodiment show in FIG. 2, the patient line is alternatively a single lumen patient line 134, which may extend to sterilizing grade filter set 100. Any of the polymer components of system 10 discussed herein, including any polymer portions of PCM devices 50*a* and 50*b,* may be made of any one or more plastic, such as, polystyrene ("PS"), polycarbonate ("PC"), blends of polycarbonate and acrylonitrile-butadiene-styrene ("PC/ABS"), polyvinyl chloride ("PVC"), polyethylene ("PE"), polypropylene ("PP"), polyesters like polyethylene terephthalate ("PET"), polyurethane ("PU") or polyetheretherketone ("PEEK").

FIG. 1A further illustrates that cycler 20 of system 10 includes a combination of PCM devices 50*a* and 50*b*. PCM devices 50*a* and 50*b* actually operate as three PCM devices or purposes, including an underheated fluid PCM device (device 50*a*), an overheated fluid PCM device (device 50*b*) and a recover effluent energy PCM device (device 50*a*). In the illustrated embodiment, the underheated fluid PCM device and the recover effluent energy PCM device are the same PCM device 50*a* having the same melting temperature, e.g., 32° C. to 34° C. The same PCM device 50*a* for addressing underheating is used at a time when the PCM has been melted and is in condition to return latent heat. The same PCM device 50*a* for recovering effluent energy is used at a time when the PCM is in solid form and is in condition to absorb latent heat from used PD fluid to melt and thereby be ready to return latent heat to underheated fresh PD fluid. Overheated fluid PCM device 50*b* is separate from dual function PCM device 50*a* and has a different melting temperature, e.g., 37° C. or higher.

It should be appreciated that cycler 20 of system 10 may instead (i) use only PCM device 50*a* for only one purpose (addressing underheating or recovering effluent energy), (ii) use only PCM device 50*a* for dual purposes (addressing underheating and recovering effluent energy), (iii) use PCM device 50*a* for only one purpose in combination with PCM device 50*b* to address overheating, or (iv) use only PCM device 50*b* to address overheating. System 10 expressly includes each of the above options.

PCM devices 50*a* and 50*b* of cycler 20 store thermal energy by the phase change from solid to liquid. In an embodiment, the PCM's used in devices 50*a* and 50*b* require a relatively large amount of energy to undergo the solid-to-liquid phase change. The energy required to transition between solid and liquid phases is known as the latent heat of fusion. The PCM's used herein have a high latent heat of fusion in one embodiment and can therefore store a significant amount of heat during a phase transition, while maintaining a near constant temperature around the PCM's melting temperature. Different PCM's for the different uses (i) to (iii) above are chosen to have a desired melting temperature for that use.

The melting temperature in an embodiment dictates the material and type of PCM suitable for use in the system of the present disclosure. Because the melting temperatures needed here are relatively low, paraffin or paraffin blend waxes and non-paraffin organics are suitable because they are relatively inexpensive and remain stable through many thermal cycles. Paraffins (paraffin blends) and non-paraffin organics are suitable PCM's because they melt and freeze congruently (have the same composition before and after freezing) and therefore provide material stability through many treatments, making the PCM devices of the present disclosure largely reusable. A draw back of paraffin (paraffin blend) and non-paraffin organic PCM's is their thermal conductivity, which may be around 0.2 W/m-K. It is accordingly contemplated to form or place the PCM within a series or matrix of conductive heat fins for devices 50*a* and 50*b* as discussed in connection with FIGS. 6A and 6B below.

Referring still to FIG. 1A, for the embodiment in which it is intended that underheating by inline PD fluid heater 32 is mitigated, e.g., at the beginning of a patient fill, PCM device 50*a* may be placed between inline PD fluid heater 32 and a downstream temperature sensor 30*b,* so that the temperature increasing effect from PCM device 50*a* is detected or recorded by the downstream temperature sensor. To increase the temperature of underheated fresh PD fluid, PCM device 50*a* prior to the patient fill is heated and melted. The melting temperature for the underheated fluid PCM device is in one embodiment 32° C. to 34° C. Here, the fresh PD fluid flowing past the melted underheated fluid PCM device at a temperature lower than 32° C. to 34° C. will freeze the melted PCM, releasing the latent heat from the PCM and warming the fresh PD fluid to the melting temperature, e.g., 32° C. to 34° C.

As the inline fluid heating stabilizes and begins to output fresh PD fluid closer to the commanded temperature of 37° C., the PCM of underheated fluid PCM device 50*a* remelts, pulling latent heat into the device. Underheated fluid PCM device 50*a* accordingly creates a lag in PD fluid temperature. Eventually, the PCM of PCM device 50*a* is fully melted and thereafter has no further effect on PD fluid temperature unless the temperature during the patient fill for some reason falls again below the melting temperature for underheated fluid PCM device 50*a,* e.g., 32° C. to 34° C.

As stated above, the PCM for underheated fluid PCM device 50*a* of system 10 is heated and melted prior to beginning the patient fill. It is contemplated to do this in a plurality of different ways. In one way illustrated in FIG. 6B, underheated fluid PCM device 50*a* is provided with one or more heating element positioned to heat the heat fins of the device, which in turn heat and melt the PCM prior to a patient fill. The heating may be performed just prior to the beginning of the patient fill.

In a second way, which may be performed for a first patient fill that does not follow an initial patient drain, system 10 heats priming fluid and flows the heated priming fluid through underheated fluid PCM device 50*a* to melt the PCM prior to a first patient fill. Here, control unit 40 toggles three-way valve 126 to allow heated priming fluid to flow from inline PD fluid heater 32 and through PCM device 50*a,* with used PD fluid valve 26*b* closed and valves 26*a* and 26*c* open. Heated priming fluid flows from top to bottom in PCM device 50*a* as shown in FIG. 1A.

In a third way, which may be performed for a first patient fill that does follow an initial patient drain, or for any subsequent fill that follows a patient drain, system 10 recovers heat from the patient's effluent or used PD fluid. The patient's effluent, which typically has a body temperature, e.g., 37° C. is flowed through underheated fluid PCM device 50*a* to melt the PCM prior to the subsequent patient fill. Here, control unit 40 toggles three-way valve 126 to allow the patient's effluent, flowing right to left in FIG. 1A through PCM device 50*a,* to bypass inline PD fluid heater 32 via bypass line 18*y,* with used PD fluid valve 26*b* open and valves 26*a* and 26*c* closed. Used PD fluid flows from bottom to top in PCM device 50*a* as shown in FIG. 1A. The direction of PD fluid flow through PCM devices 50*a* and 50*b* accordingly does not matter in one embodiment of system 10 of the present disclosure.

FIG. 1A also illustrates that for the embodiment in which overheating by the inline PD fluid heater is mitigated, e.g., during a no or low PD fluid flow condition, that PCM device 50*b* may also be placed between inline PD fluid heater 32 and downstream temperature sensor 30*b,* so that the temperature decreasing effect from PCM device 50*b* is detected or recorded by the downstream temperature sensor. To decrease the temperature of overheated fresh PD fluid, the PCM of PCM device 50*b* melts to absorb latent heat, thereby lowering the temperature of the fresh PD fluid. The melting temperature for overheated fluid PCM device 50*b* is in one embodiment 37° C. but could be higher if a slight overtemperature is acceptable, e.g., to reduce the amount of thermal cycles to which PCM device 50*b* is subjected. Here, the fresh PD fluid flowing past the solid overheated fluid PCM device 50*b* at a temperature greater than 37° C. (or higher setpoint) melts its PCM, causing heat to be stored by the PCM and cooling the fresh PD fluid to the melting temperature, e.g., 37° C. or higher.

To pump PD fluid through overheated fluid PCM device 50*b,* control unit 40) causes valves 26*a* and 26*c* to be opened and three-way valve 126 to be toggled so that PD fluid exiting heater flows through underheated fluid PCM device 50*a,* valve 26*c*. overheated fluid PCM device 50*b,* valve 26*a* and fresh PD fluid line 18*a* to patient P via fresh PD fluid lumen 36*a* of dual lumen patient line 34. Since the fresh PD fluid is here overheated, the melted PCM of underheated fluid PCM device 50*a* has no effect.

FIG. 1A further illustrates that for the embodiment in which it is desired to remove heat from the patient's effluent or used PD fluid, e.g., to produce an overall more energy efficient PD system 10, PCM device 50*a,* via open valve 26*b* and closed valve 26*c* is able to communicate fluidly with effluent or used PD fluid return line 18*b* within cycler 20, which in turn communicates fluidly with used PD fluid lumen 36*b* of dual lumen patient line 34 from which used PD fluid or effluent is removed from patient P. Control unit 40) causes PD fluid pump 24 to pump used PD fluid or effluent through opened drain valve 26*n* to a house drain or drain container via a drain line 18*d.* Recover effluent energy PCM device 50*a* operates in the same manner as the overheated fluid PCM device 50*b,* wherein the PCM melts from a solid to a liquid to remove heat from the PD fluid and absorb the latent heat within the PCM. Here, however, the melting temperature of recover effluent energy PCM device 50*a* is lower, e.g., 32° C. to 34° C. (e.g., the same as above for underheated fluid PCM device 50*a*), so that the PCM is melted by the patient's effluent, which is at body temperature or 37° C. In FIG. 1A, recover effluent energy PCM device 50*a* is located within cycler 20 so that it may later receive fresh PD fluid to transfer the stored latent heat to the fresh PD fluid, thereby recovering and returning energy from the effluent fluid.

In the embodiment of system 10 in which only PCM device 50*a* is provided and is used primarily to recoup energy from used PD fluid or effluent, PCM device 50*a* may still be located in the positon shown in FIG. 1A. In this manner, PCM device 50*a* may contact used PD fluid to remove heat at one time (patient drain) and contact fresh PD fluid to deliver heat at a second time (patient fill).

Figure 1B:
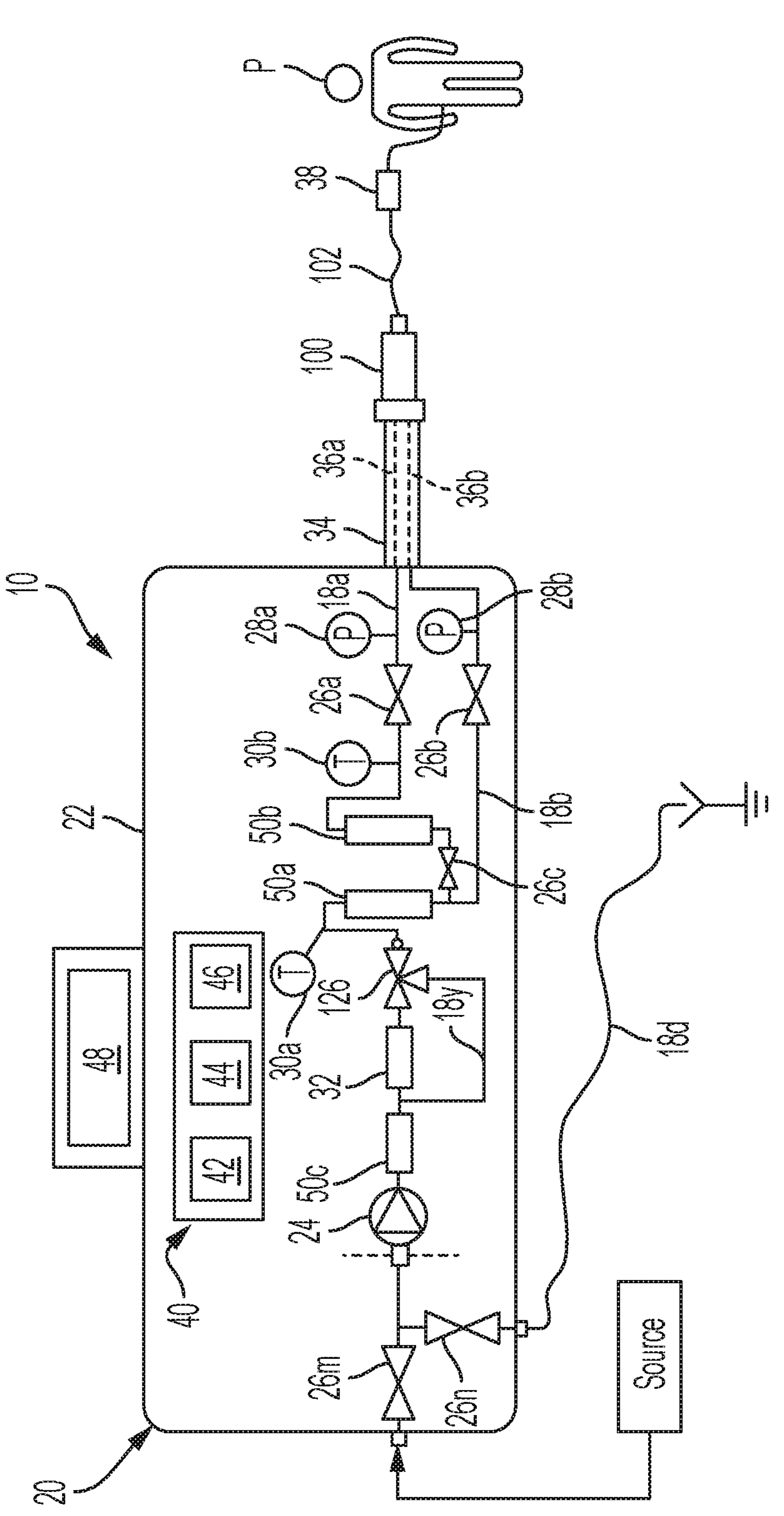
FIG. 1B is a schematic view of an alternative embodiment for a dual lumen patient line peritoneal dialysis system having at least one phase change material ("PCM") device of the present disclosure.

Referring now to FIG. 1B, where a PCM device is provided to recoup energy from used PD fluid or effluent, PCM device 50*c* may be provided by itself (PCM devices 50*a,* 50*b* are not provided), provided along with only one of PCM device 50*a* or PCM device 50*b,* or provided along with both PCM devices 50*a,* 50*b* as illustrated in FIG. 1B. In FIG. 1B, recover effluent energy PCM device 50*c* is located within cycler 20 so that it may later receive fresh PD fluid to transfer the stored latent heat to the fresh PD fluid, thereby recovering and returning energy from the effluent fluid. In the illustrated embodiment, PCM device 50*c* is located upstream of inline PD fluid heater 32 and the return of bypass line 18*y.* Locating PCM device 50*c* upstream of inline PD fluid heater 32 allows the melting temperature of the corresponding PCM to be considerably lower, e.g., 25° C. to 30° C., increasing the amount of latent energy that may be stored from the flowing patient effluent (and later recovered), wherein the effluent fluid may be at or near body temperature or 37° C. During a next patient fill, fresh, unheated PD fluid at a known or expected temperature below the PCM melting temperature (e.g., 25° C. to 30° C.), causes the melted PCM to start to solidify, giving off heat and warming the incoming fresh PD fluid.

In some embodiments, PCM device 50*c* may be used in conjunction with PCM device 50*a*. PCM device 50*c* may be located downstream from PCM device 50*a.* In these embodiments, PCM device 50*a* would first melt by the warm PD fluid, having a melting temperature of, for example, 32° C. to 34° C. The solution would then pass the PCM device 50*c,* with a lower meting point than PCM device 50*a,* for example, 25° C. to 30° C., further storing the latent energy.

Figure 2:
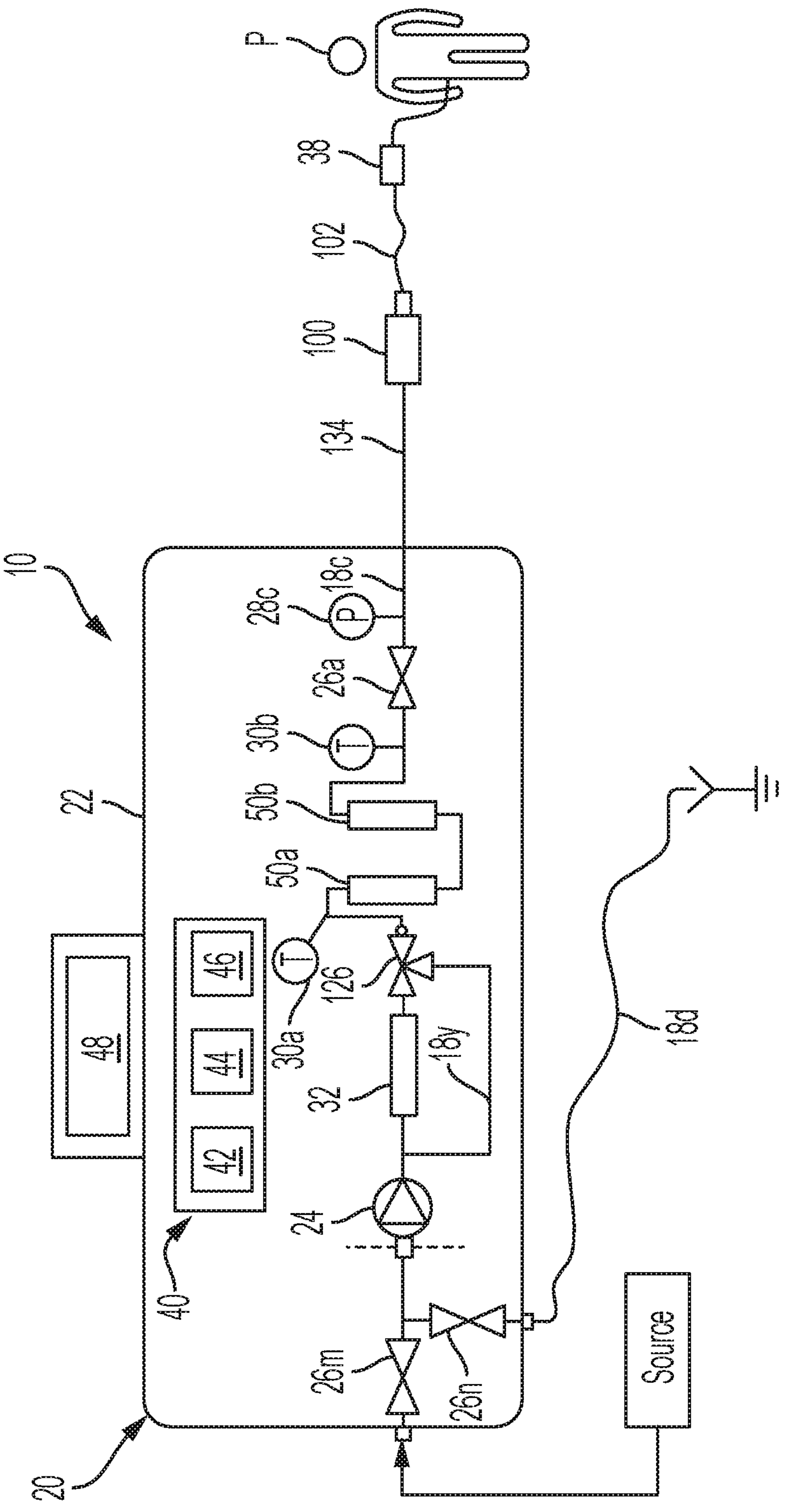
FIG. 2 is a schematic view of one embodiment for a single lumen patient line peritoneal dialysis system having at least one PCM device of the present disclosure.

Referring now to FIG. 2, system 10 is shown as being configured alternatively to operate with a single fresh and used PD fluid line 18*c* and a single lumen patient line 134, which may again include a sterilizing grade filter set 100. Sterilizing grade filter set 100 here includes internal pathways and valves, such as check valves that allow the used PD fluid to bypass and not clog a filter membrane located within sterilizing grade filter set 100. One such sterilizing grade filter set is disclosed in U.S. Patent Publication No. 2020/0086028, assigned to the assignee of the present disclosure, the entire contents of which are incorporated herein by reference and relied upon. A short, flexible tube 102 may again be provided to extend form sterilizing grade filter set 100 to the patient's transfer set 38. Pressure sensors 28*a* and 28*b* in system 10 of FIGS. 1A and 1B are replaced by a single pressure sensor 28*c* in system 10 of FIG. 2. Bypass three-way valve 126 may again be provided so that effluent or used PD fluid does not have to flow through inline PD fluid heater 32, which may clog the heater with fibrin, proteins and other patient materials, and may instead flow along bypass line 18*y* to PD fluid pump 24. If it is found that effluent or used PD fluid does not negatively affect the operation of inline PD fluid heater 32, even over time, three-way valve 126 may be eliminated in system 10 of both FIGS. 1 and 2. It should also be appreciated that one or more additional three-way valve may be used elsewhere within PD machine or cycler 20, e.g., as a replacement for two single direction valves where the two valves would not have to be open or closed at the same time.

PCM devices 50*a* and 50*b* in single lumen patient line system 10 may be configured to have the same melting temperatures as described above in FIG. 1A for dual lumen patient line system 10. PCM devices 50*a* and 50*b* in single lumen patient line system 10 may operate in the same manners as described above in FIG. 1A for dual lumen patient line system 10. Also, single lumen patient line system 10 of FIG. 2 may (i) use both PCM devices 50*a* and 50*b* for all three purposes (addressing underheating and overheating and recovering effluent energy), (ii) use only PCM device 50*a* for only one purpose (addressing underheating or recovering effluent energy), (iii) use only PCM device 50*a* for dual purposes (addressing underheating and recovering effluent energy), (iv) use PCM device 50*a* for only one purpose in combination with PCM device 50*b* to address overheating, or (v) use only PCM device 50*b* to address overheating. System 10 of FIG. 2 expressly includes each of the above options.

It should be appreciated that PCM device 50*c* of FIG. 1B may be additionally or alternatively provided in system 10 of FIG. 2. Here again, PCM device 50*c* is located between PD fluid pump 24 and inline PD fluid heater 32 and includes each of the structure, functionality and alternatives discussed above in connection with FIG. 1B.

Figure 3:
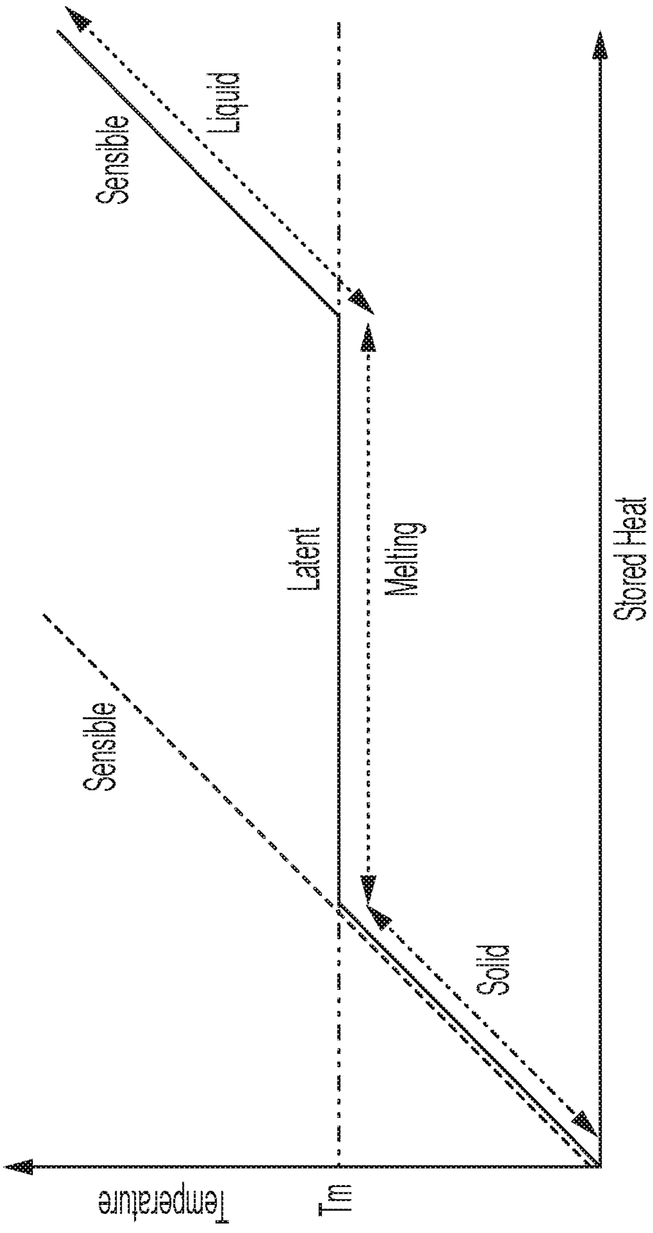
FIG. 3 is a graph illustrating the thermodynamic operation of the PCM devices of the present disclosure.

FIG. 3 graphically illustrates the operation of the PCM of PCM devices 50*a* to 50*c*. In FIG. 3, latent heat (horizontal arrow) is the energy absorbed or released by a thermodynamic system (PCM of PCM devices 50*a* to 50*c*) during a constant temperature process. When a solid melts (turns into a liquid) or a liquid evaporates (turns into a gas) energy is absorbed (pulled from fresh or used PD fluid to cool same) because the loosening of the attraction among the molecules requires energy. An example of latent heat being absorbed is ice melting. When a melted fluid solidifies (freezes) energy is released (transferred to fresh PD fluid to heat same) because the tightening of the attraction among the molecules releases energy. FIG. 3 also shows two examples of sensible heat (diagonal arrows). Sensible heat is heat exchanged by a thermodynamic system in which temperature changes without changing some variables, such as volume or pressure.

Figure 4:
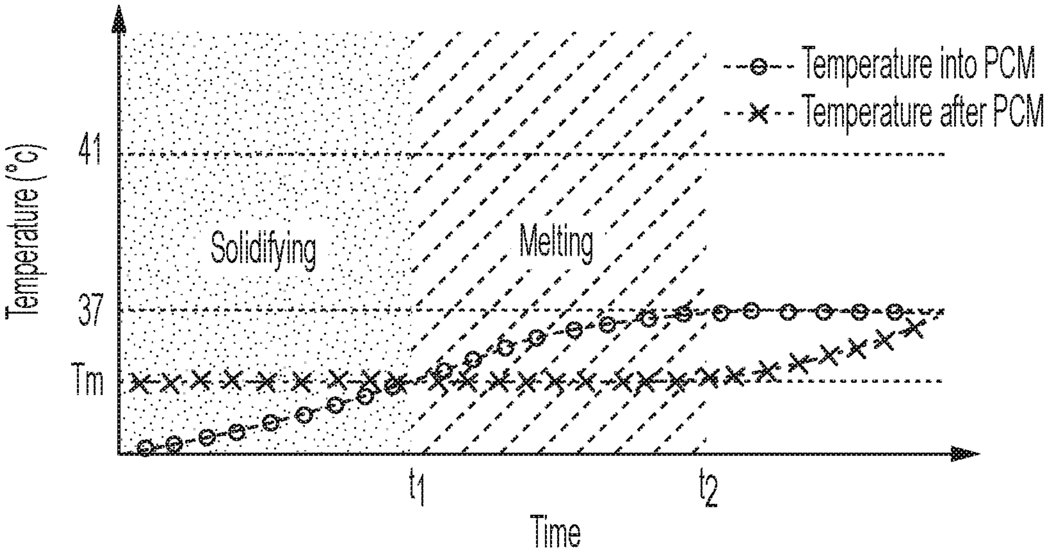
FIG. 4 is a graph illustrating an example temperature versus time output using an underheated fluid PCM device of the present disclosure.

FIG. 4 graphically illustrates an example temperature versus time output of system 10 using underheated fluid PCM device 50*a*. Here, stored heat is released during the start of a patient fill when cold or underheated fresh PD fluid solution (circle-line curve) with a temperature of below the melting temperature ("Tm") enters PCM device 50*a*. The PCM of device 50*a* starts to solidify, releasing the latent heat stored and heating fresh PD fluid to the melting temperature Tm. When the temperature of fresh PD fluid entering PCM device 50*a* (circle-line curve) is heated above the melting temperature Tm (at time $t_1$), the PCM of PCM device 50*a* starts to melt again, which results in the benefit that the fresh PD fluid delivered to the patient (x-line curve) does not fall below the melting temperature Tm. A slight drawback is that the fresh PD fluid exiting PCM device 50*a* (x-line curve) remains at a lower than commanded temperature (e.g., 37° C.) for a longer period of time, e.g., even during PCM melting as shown in FIG. 4, such that during PCM melting the incoming PD fluid temperature (circle-line curve) may actually be higher than the exiting PD fluid temperature (x-line curve). The material and dimensions (e.g., diameter and length) of the PCM of device 50*a* (see FIGS. 6A and 6B) are chosen, however, to maximize the desired thermal properties and capacity and to minimize the lag to reach commanded temperature. For example, in an embodiment in which system 10 relies on a thermal disinfection after treatment, the PCM is selected to have the physical properties that can withstand disinfection cycles over the lifetime of system 10, or at least over a service cycle for the PCM. At the completion of PCM melting at time $t_2$ in the example of FIG. 4, the temperature of fresh PD fluid exiting PCM device 50*a* (x-line curve) quickly rises to the commanded temperature (e.g., 37° C.).

Figure 5:
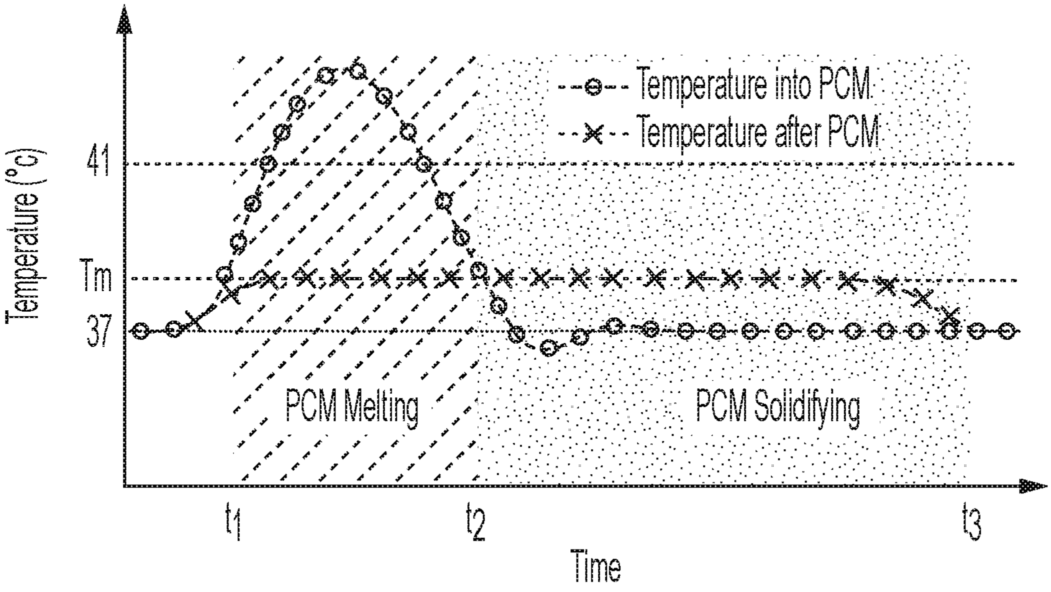
FIG. 5 is a graph illustrating an example temperature versus time output using an overheated fluid PCM device of the present disclosure (which looks the same for the recover effluent energy PCM device).

FIG. 5 graphically illustrates an example temperature versus time output of system 10 using overheated fluid PCM devices 50*b*, 50*c*. Here, overheated fluid PCM devices 50*b*, 50*c* dampen the incoming PD fluid temperature spike (circle-line curve) above the PCM melting temperature Tm. The temperature of fresh PD fluid exiting PCM devices 50*b*, 50*c* (x-line curve) during the PCM melting period (between times $t_1$ and $t_2$) is effectively clamped at the PCM melting temperature Tm, which may be only slightly higher than the commanded temperature (e.g., 37° C.) as discussed herein, helping to prevent patient discomfort due to the delivery of overheated PD fluid. During the phase between times $t_1$ and $t_2$ in which the incoming fluid temperature (circle-line curve) is above the melting temperature Tm, the PCM of PCM devices 50*b*, 50*c* melts and thereby stores excessive energy as latent heat. The temperature of fresh PD fluid (circle-line curve) entering overheated fluid PCM devices 50*b*, 50*c* may drop below the melting temperature Tm (between times $t_2$ and $t_3$) due for example to the temperature feedback algorithm at control unit 40 overcompensating for the overtemperature. Here (between times $t_2$ and $t_3$), the PCM of devices 50*b*, 50*c* solidifies, releasing the latent heat and heating the fresh PD fluid to the melting temperature Tm. The temperature of PD fluid exiting PCM devices 50*b*, 50*c* (x-line curve) during the solidifying between times $t_2$ and $t_3$ is accordingly held to the melting temperature Tm. After solidification (after time $t_3$), the exiting fresh PD fluid temperature (x-line curve) drops to the commanded temperature (e.g., 37° C.).

Figure 6A:
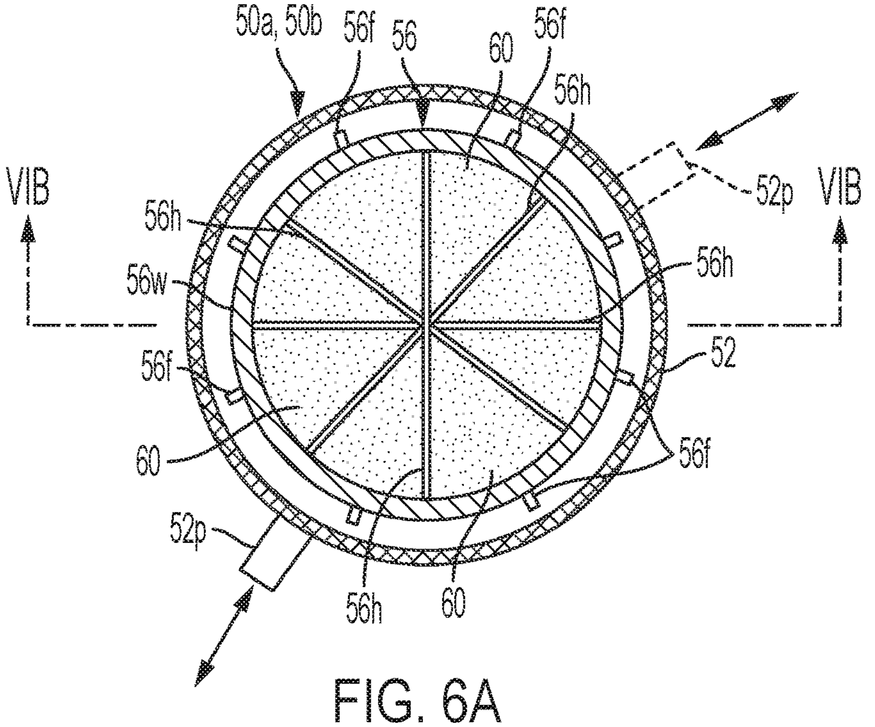
FIG. 6A is a top plan section view of one embodiment of a PCM device of the present disclosure taken along line VIA-VIA of FIG. 6B.
Figure 6B:
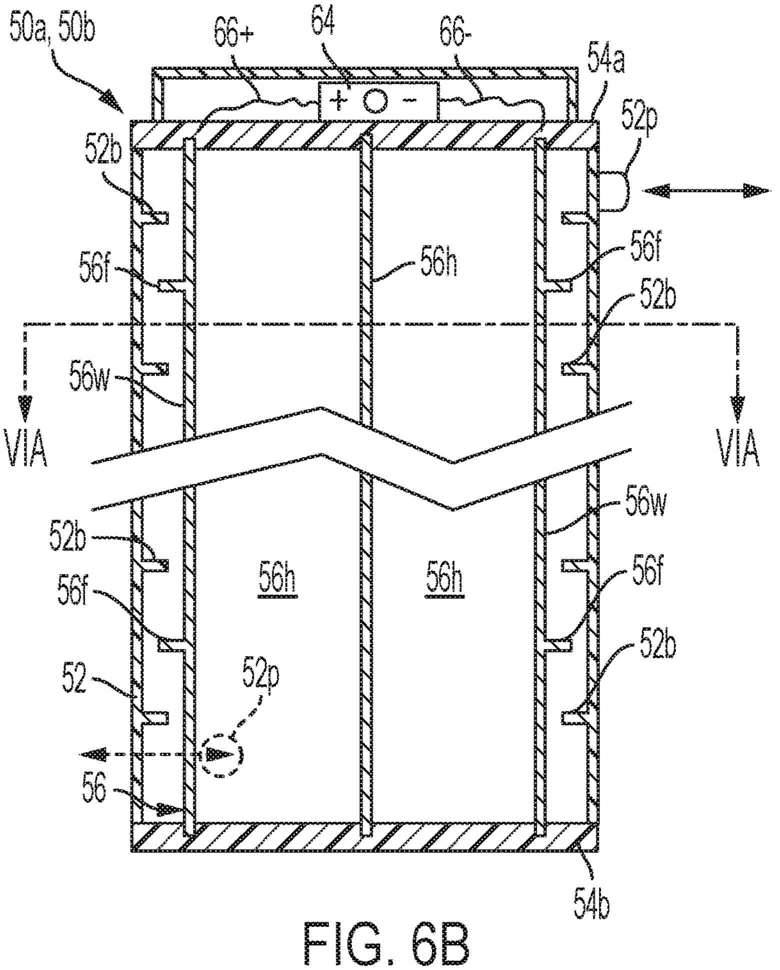
FIG. 6B is a front elevation section view of one embodiment of a PCM device of the present disclosure taken along line VIB-VIB of FIG. 6A.

Referring now to FIGS. 6A and 6B, an embodiment for PCM devices 50*a* to 50*c* is illustrated. PCM devices 50*a* to 50*c* include an outer shell 52, which may be cylindrical and be made of any of a thermally insulating material, such as any of the polymers listed herein (e.g., PS, PC, PC/ABS, PVC, PE, PP, PET, PU or PEEK). Outer shell 52 may alternatively be made of a thermally conductive material depending on the application of PCM device 50*a* to 50*c*, such as stainless steel, which is suitable for contacting PD fluid. In any case, outer shell 52 is sealed to caps 54*a*, 54*b*, e.g., ultrasonically, thermally and/or adhesively such as solvent bonding (or welded and/or press-fit if made of a conductive material). Outer shell 52 includes inlet and outlet ports 52*p,* which may each at one time act as an inlet port and at another time act as an outlet port. Fresh or used PD fluid may accordingly flow from the top to the bottom of outer shell 52 in FIG. 6B or from the bottom to the top of outer shell 52 in FIG. 6B.

As illustrated in FIGS. 6A and 6B, outer shell 52 surrounds a PCM holding core 56. PCM holding core 56 includes a conductive cylindrical wall 56*w* that holds a PCM 60 having a desired formulation and melting temperature, e.g., 32° C. to 34° C. for PCM device 50*a,* 37° C. or higher for PCM device 50*b,* and 25° C. to 30° C. for PCM device 50*c.* Conductive cylindrical wall 56*w* contacts fresh and possibly used PD fluid and may accordingly be made of stainless steel, which is conductive and medically safe. In the illustrated embodiment, cylindrical wall 56*w* includes or contacts a plurality of internal heat fins 56*h,* which are non-PD fluid contacting, such that the heat fins may be of a highly thermally conductive material, such as aluminum or copper. Heat fins 56*h* also hold PCM 60 in place when in its liquid form, so that it will freeze back into generally the same shape abutting against heat fins 56*h* and cylindrical wall 56*w.* Internal heat fins 56*h* as illustrated contact and are in thermal communication with conductive cylindrical wall 56*w.* Internal heat fins 56*h* help to transfer heat from the fresh or used PD fluid to PCM 60 and to transfer heat from PCM 60 to the fresh or used PD fluid depending on the application. In FIG. 6B, conductive cylindrical wall 56*w* and internal heat fins 56*h* embed slightly into caps 54*a,* 54*b* to hold core 56 firmly in place within outer shell 52 and to prevent fresh or used PD fluid from contacting PCM 60.

The diameters and lengths of outer shell 52 and PCM holding core 56 are chosen to provide an amount of PCM 60 that has an at least adequate capacity for latent heat with which to handle the applications described herein. The amount of PCM 60 is also chosen to withstand numerous thermal cycles over multiple, multiple PD treatments. It is contemplated that the volume of PCM 60 provided in devices 50*a* to 50*c* is optimized based on a number of factors, such as its intended purpose, the expected temperature delta, the internal volume of the flow path between inline PD fluid heater 32 and the PCM device, and the design of inline PD fluid heater 32.

In the illustrated embodiment, cylindrical wall 56*w* also includes or is attached to a plurality of outer heat fins 56*f,* which are PD fluid contacting, such that the heat fins may made be of a thermally conductive and medically safe material, such as stainless steel. Outer heat fins 56*f* as illustrated contact and are in thermal communication with conductive cylindrical wall 56*w.* Outer heat fins 56*f* also help to transfer heat from the fresh or used PD fluid to PCM 60 and to transfer heat from PCM 60 to the fresh or used PD fluid depending on the application. In FIG. 6A, outer heat fins 56*f* are illustrated as extending generally vertically, while in FIG. 6B, outer heat fins 56*f* are illustrated as extending generally horizontally. FIG. 6B also illustrates that generally horizontally extending heat fins 56*f* in an embodiment cooperate with baffles 52*b* extending generally inwardly from outer shell 52. Heat fins 56*f* and baffles 52*b* disrupt flow and create a serpentine like fresh or used PD fluid flow between inlet and outlet ports 52*p* (in either direction). The disrupted flow creates turbulence, which aids heat transfer and increases the contact time between the fresh or used PD fluid and conductive cylindrical wall 56*w.* Different turbulators may be used instead, such as a toroidal spring-like circular ramp located between outer shell 52 and conductive cylindrical wall 56*w* that causes fresh or used PD fluid to swirl around conductive cylindrical wall 56*w* as it flows up or down from inlet port 52*p* to outlet port 52*p.*

FIG. 6B further illustrates that as discussed herein, PCM devices 50*a* to 50*c* of PD system 10 of the present disclosure may include one or more heating element 64, e.g., in thermal communication with conductive cylindrical wall 56*w* and the matrix of heat fins 56*h*. Control unit 50 is programmed to actuate one or more heating element 64 to melt PCM 60 prior to a use application in which fresh PD fluid is to be heated. In the illustrated embodiment, one or more leads 66+ and 66– (which are suitably electrically isolated from any fresh or used PD fluid flowing through the PCM device to provide at least Class II operation) extends from heating element 64 to conductive cylindrical wall 56*w,* which is in turn in contact and thermal communication with the matrix of heat fins 56*h.* The electrical resistance associated with conductive cylindrical wall 56*w* and heat fins 56*h* causes same to heat when electrical current is applied by heating element 64. Heat is conducted to PCM 60, which melts the PCM to place it in condition to heat fresh PD fluid. Although not illustrated, PCM devices 50*a* to 50*c* may include a temperature sensor that outputs to control unit 50, wherein the temperature sensor includes one or more probe that extends into PCM 60, so that it is known when the PCM has reached its melting temperature.

In an alternative embodiment, PCM device 50*c* (recouping effluent heat to heat or preheat (see FIG. 1B) incoming fresh PD fluid) is formed as a heat exchanger. The heat exchanger is in one embodiment formed having an outer insulating, e.g., plastic (any listed herein) or fiberglass, shell. The shell is cylindrical in one embodiment. Two conductive tubes, e.g., stainless steel, are provided within the shell, one for carrying fresh PD fluid and the other for carrying used PD fluid. PCM material having the desired melting temperature, e.g., 25° C. to 30° C., for recovering effluent energy is then provided (e.g., molded or poured) within the insulating shell and around the outsides of the fresh and used PD fluid tubes, which may be juxtaposed in parallel. The heat exchanger works even when the fresh and used PD fluids do not flow at the same time (e.g., for a continuous cycling PD ("CCPD") treatment) because the insulated PCM material stores the latent heat energy absorbed from the effluent fluid until fresh PD fluid is flowed through its tube in the next patient fill. In one embodiment, control unit 40 of PD machine or cycler 20 is programmed to begin the next patient fill directly after the completion of a patient drain to reduce overall treatment time, which helps the PCM material to hold the latent heat energy until it can be transferred to incoming fresh PD fluid.

It should be understood that various changes and modifications to the presently preferred embodiments described herein will be apparent to those skilled in the art. It is therefore intended that any or all of such changes and modifications may be covered by the appended claims. For example, while the recovery of heat from effluent or used PD fluid using a PCM device of the present disclosure is described in connection with inline heating, such a PCM device may be used equally as effectively with batch PD fluid heating. Other applications for the recovery of heat may include the recovery of heat after disinfection in PD system 10, a water purification unit or a hemodialysis machine. In another example, it is contemplated to provide a second, heat storage fluid loop that includes a second fluid pump. PCM device 50*a* feeds one side of a heat exchanger, while the heat storage fluid loop includes the second side of the heat exchanger. The heat storage fluid loop stores the energy after a heat disinfection of the primary treatment loop including PCM device 50*a* without impacting the disinfection time and allowing cool down time to be reduced.

The invention is claimed as follows:

1. A peritoneal dialysis ("PD") system comprising:

a PD fluid pump;

a PD fluid heater positioned and arranged to heat fresh PD fluid pumped by the PD fluid pump; and a phase change material ("PCM") device positioned and arranged to receive the fresh PD fluid that is heated by the PD fluid heater, the PCM device including a PCM having a melting temperature selected so that the PCM solidifies when the fresh PD fluid is underheated and contacts the PCM, transferring heat to the underheated fresh PD fluid, wherein the PCM device is further positioned to receive used PD fluid, the melting temperature of the PCM selected so that the PCM melts when the used PD fluid contacts the PCM, removing heat from the used PD fluid.

2. The PD system of claim 1, wherein the PD fluid heater is an inline heater.

3. The PD system of claim 1, wherein the melting temperature for the PCM is below 37° C.

4. The PD system of claim 1, wherein the underheated fresh PD fluid is PD fluid having a temperature below the melting temperature.

5. The PD system of claim 1, wherein the PCM is configured to further melt, prior to the underheated fresh PD fluid contacting the PCM, using one or more heating element provided with the PCM device.

6. The PD system of claim 1, further comprising a bypass line enabling the used PD fluid to bypass the PD fluid heater.

7. The PD system of claim 1, further comprising a dual lumen patient line, and wherein a PD machine housing the PD fluid pump, the PD fluid heater, and the PCM device further includes:

(i) a fresh PD fluid line for fluid communication with a fresh PD fluid lumen of the dual lumen patient line, (ii) a used PD fluid line for fluid communication with a used PD fluid lumen of the dual lumen patient line, and (iii) at least one valve positioned and arranged to selectively allow (a) the fresh PD fluid to flow through the PCM device, the fresh PD fluid line, and the fresh PD fluid lumen and (b) the used PD fluid to flow through the used PD fluid lumen, the used PD fluid line, and the PCM device.

8. The PD system of claim 1, further comprising a single lumen patient line, and wherein a PD machine housing the PD fluid pump, the PD fluid heater, and the PCM device further includes a fresh and used PD fluid line for fluid communication with the single lumen patient line, the fresh and used PD fluid line positioned and arranged to accept the fresh PD fluid from the PCM device and deliver the used PD fluid to the PCM device.

9. The PD system of claim 1, wherein the PCM device is a first PCM device, and which includes a second PCM device including a second PCM having a second melting temperature selected so that the second PCM melts when the fresh PD fluid is overheated and contacts the second PCM, removing heat from the overheated fresh PD fluid.

10. The PD system of claim 9, wherein the second PCM device is located downstream from the first PCM device in a direction of flow of the fresh PD fluid.

11. The PD system of claim 9, wherein the second melting temperature for the second PCM is 37° C. or higher.

12. The PD system of claim 1, wherein the PCM device is positioned upstream of the PD fluid heater so as to receive the used PD fluid.

13. The PD system of claim 12, wherein the melting temperature of the PCM is between 25° C. to 30° C.

14. A peritoneal dialysis ("PD") system comprising:

a PD fluid pump;

a PD fluid heater positioned and arranged to heat fresh PD fluid pumped by the PD fluid pump; and a phase change material ("PCM") device positioned and arranged to receive the fresh PD fluid that is heated by the PD fluid heater, the PCM device including:

a PCM having a melting temperature selected so that the PCM solidifies when the fresh PD fluid is underheated and contacts the PCM, transferring heat to the underheated fresh PD fluid, and a conductive wall configured to separate the PCM from heated priming fluid or used PD fluid, wherein the PD system is configured to melt the PCM prior to the underheated fresh PD fluid contacting the PCM, the melting caused by flowing the heated priming fluid past the PCM or flowing the used PD fluid past the PCM.

15. The PD system of claim 14, wherein the melting temperature for the PCM is below 37° C.

16. A peritoneal dialysis ("PD") system comprising:

a PD fluid pump;

a PD fluid heater positioned and arranged to heat fresh PD fluid pumped by the PD fluid pump;

a phase change material ("PCM") device positioned and arranged to receive the fresh PD fluid that is heated by the PD fluid heater, the PCM device including a PCM having a melting temperature selected so that the PCM solidifies when the fresh PD fluid is underheated and contacts the PCM, transferring heat to the underheated fresh PD fluid;

a dual lumen patient line;

a fresh PD fluid line for fluid communication with a fresh PD fluid lumen of the dual lumen patient line;

a used PD fluid line for fluid communication with a used PD fluid lumen of the dual lumen patient line; and at least one valve positioned and arranged to selectively allow (a) the fresh PD fluid to flow through the PCM device, the fresh PD fluid line, and the fresh PD fluid lumen, and (b) the used PD fluid to flow through the used PD fluid lumen, the used PD fluid line, and the PCM device.

17. The PD system of claim 16, wherein the melting temperature for the PCM is below 37° C.

18. A peritoneal dialysis ("PD") system comprising:

a PD fluid pump;

a PD fluid heater positioned and arranged to heat fresh PD fluid pumped by the PD fluid pump;

a phase change material ("PCM") device positioned and arranged to receive the fresh PD fluid that is heated by the PD fluid heater, the PCM device including a PCM having a melting temperature selected so that the PCM solidifies when the fresh PD fluid is underheated and contacts the PCM, transferring heat to the underheated fresh PD fluid;

a single lumen patient line; and a fresh and used PD fluid line for fluid communication with the single lumen patient line, the fresh and used PD fluid line positioned and arranged to accept the fresh PD fluid from the PCM device and deliver used PD fluid to the PCM device.

19. A peritoneal dialysis ("PD") system comprising:
a PD fluid pump;
a PD fluid heater positioned and arranged to heat fresh PD fluid pumped by the PD fluid pump;
a first phase change material ("PCM") device positioned and arranged to receive the fresh PD fluid that is heated by the PD fluid heater, the first PCM device including a first PCM having a melting temperature selected so that the first PCM solidifies when the fresh PD fluid is underheated and contacts the first PCM, transferring heat to the underheated fresh PD fluid; and
a second PCM device including a second PCM having a second melting temperature selected so that the second PCM melts when the fresh PD fluid is overheated and contacts the second PCM, removing heat from the overheated fresh PD fluid.

20. The PD system of claim 19, wherein the second PCM device is located downstream from the first PCM device in a direction of flow of the fresh PD fluid.

21. The PD system of claim 19, wherein the second melting temperature for the second PCM is 37° C. or higher.

22. The PD system of claim 19, wherein the melting temperature for the first PCM is below 37° C.

* * * * *